US007232786B2

(12) United States Patent
Lockemeyer

(10) Patent No.: US 7,232,786 B2
(45) Date of Patent: *Jun. 19, 2007

(54) CATALYST COMPOSITION

(75) Inventor: John Robert Lockemeyer, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/936,248

(22) Filed: Sep. 8, 2004

(65) Prior Publication Data

US 2005/0085380 A1    Apr. 21, 2005

Related U.S. Application Data

(63) Continuation-in-part of application No. 09/992,784, filed on Nov. 6, 2001, which is a continuation of application No. 09/392,521, filed on Sep. 9, 1999, now abandoned.

(60) Provisional application No. 60/100,196, filed on Sep. 14, 1998.

(51) Int. Cl.
B01J 21/02 (2006.01)
B01J 27/02 (2006.01)
B01J 23/00 (2006.01)
B01J 23/70 (2006.01)
B01J 23/50 (2006.01)

(52) U.S. Cl. ............... 502/202; 502/216; 502/224; 502/300; 502/337; 502/338; 502/339; 502/340; 502/344; 502/347; 502/348; 502/302

(58) Field of Classification Search ............ 502/344, 502/347, 348, 300, 337–340, 302, 216, 202, 502/224

See application file for complete search history.

(56) References Cited

U.S. PATENT DOCUMENTS

| 2,424,083 | A | * | 7/1947 | Finch et al. ............... 502/347 |
| 2,901,441 | A | | 8/1959 | Waterman ................. 252/463 |
| 3,895,093 | A | | 7/1975 | Weidenbach et al. ..... 423/213.5 |
| 3,972,829 | A | | 8/1976 | Michalko ................. 252/430 |
| 4,005,049 | A | | 1/1977 | Fields ..................... 252/467 |
| 4,125,480 | A | | 11/1978 | Maxwell .................. 252/414 |
| 4,186,106 | A | | 1/1980 | Rebsdat et al. ........... 252/414 |
| 4,212,772 | A | | 7/1980 | Mross et al. ............. 252/476 |
| 4,235,798 | A | | 11/1980 | Bartley et al. ............ 260/449 |
| 4,244,889 | A | | 1/1981 | Bartley et al. ............ 564/132 |
| 4,356,312 | A | | 10/1982 | Nielsen et al. ............ 549/534 |
| 4,361,500 | A | | 11/1982 | Mathe et al. ............. 252/430 |
| 4,361,504 | A | | 11/1982 | Solomon et al. .......... 252/463 |
| 4,366,092 | A | | 12/1982 | Winterton ................ 252/476 |
| 4,367,167 | A | | 1/1983 | Lee et al. ................ 252/472 |
| 4,368,144 | A | | 1/1983 | Mitsuhata et al. ........ 502/348 |
| 4,379,134 | A | | 4/1983 | Weber et al. ............. 423/626 |
| 4,382,149 | A | | 5/1983 | Krueger ................. 568/473 |
| 4,420,420 | A | | 12/1983 | Mita et al. ............... 502/261 |
| 4,532,231 | A | | 7/1985 | Johnson ................. 502/347 |
| 4,628,129 | A | | 12/1986 | Bartley ................. 568/864 |
| 4,665,048 | A | | 5/1987 | Van Leeuwen et al. .... 502/221 |
| 4,797,270 | A | | 1/1989 | Alvarado Cendan et al. ................. 423/625 |
| 4,797,279 | A | | 1/1989 | Karamata et al. ......... 424/93 |
| 4,810,689 | A | | 3/1989 | Hayden ................. 502/347 |
| 4,874,739 | A | | 10/1989 | Boxhoorn ............... 502/218 |
| 4,886,917 | A | | 12/1989 | Knopf et al. ............ 568/623 |
| 4,908,343 | A | | 3/1990 | Bhasin .................. 502/218 |
| 4,916,243 | A | | 4/1990 | Bhasin et al. ............ 549/534 |
| 4,994,587 | A | * | 2/1991 | Notermann et al. ....... 549/534 |
| 4,994,588 | A | | 2/1991 | Kapicak et al. .......... 549/534 |
| 4,994,589 | A | | 2/1991 | Notermann .............. 549/534 |
| 5,037,794 | A | | 8/1991 | Magistro ............... 502/355 |
| 5,055,442 | A | | 10/1991 | Osaka et al. ............. 502/439 |
| 5,057,481 | A | | 10/1991 | Bhasin ................. 502/208 |
| 5,100,859 | A | | 3/1992 | Gerdes et al. ........... 502/439 |
| 5,112,795 | A | | 5/1992 | Minahan et al. ......... 502/324 |
| 5,157,180 | A | | 10/1992 | West et al. .............. 585/313 |
| 5,179,057 | A | | 1/1993 | Bartley ................ 502/170 |
| 5,187,140 | A | * | 2/1993 | Thorsteinson et al. .... 502/348 |
| 5,189,004 | A | | 2/1993 | Bartley ................ 502/170 |
| 5,364,826 | A | | 11/1994 | Kemp ................. 502/315 |
| 5,374,748 | A | | 12/1994 | Rizkalla ............... 549/534 |
| 5,380,697 | A | | 1/1995 | Matusz et al. ........... 502/348 |

(Continued)

FOREIGN PATENT DOCUMENTS

DE    2933950 A1    3/1981

(Continued)

OTHER PUBLICATIONS

U.S. Appl. No. 10/992,784, filed Nov. 6, 2001, Lockemeyer.

(Continued)

*Primary Examiner*—J. A. Lorengo
*Assistant Examiner*—Patricia L. Hailey

(57) ABSTRACT

There is provided a catalyst carrier comprising a refractory inorganic material having a sodium solubilization rate no greater than 5 ppmw/5 minutes. There is further a catalyst comprising a refractory inorganic material carrier having a sodium solubilization rate no greater than 5 ppmw/5 minutes; and one or more catalytically reactive metals deposited on said carrier. There is also provided a catalyst suitable for the vapor phase production of alkylene oxide from olefins and oxygen comprising an alumina-based carrier having a sodium solubilization rate no greater than 5 ppmw/5 minutes; and catalytically reactive silver deposited on said carrier.

28 Claims, No Drawings

U.S. PATENT DOCUMENTS

| | | | |
|---|---|---|---|
| 5,380,885 A | 1/1995 | Kemp | 549/536 |
| 5,387,751 A | 2/1995 | Hayden et al. | 549/534 |
| 5,418,202 A | 5/1995 | Evans et al. | 502/348 |
| 5,447,897 A | 9/1995 | Kemp | 502/303 |
| 5,486,628 A | 1/1996 | Kemp | 549/536 |
| 5,545,603 A | 8/1996 | Kemp | 502/347 |
| 5,597,773 A | 1/1997 | Evans et al. | 502/348 |
| 5,663,385 A | 9/1997 | Kemp | 549/536 |
| 5,668,077 A | 9/1997 | Klopries et al. | 502/347 |
| 5,703,253 A | 12/1997 | Evans et al. | 549/536 |
| 5,734,068 A | 3/1998 | Klopries et al. | 549/536 |
| 5,739,075 A * | 4/1998 | Matusz | 502/302 |
| 5,935,894 A | 8/1999 | Kanazirev | 502/341 |
| 6,103,916 A | 8/2000 | Takada et al. | 549/534 |
| 6,281,160 B1 | 8/2001 | Basset et al. | 502/332 |
| 6,368,998 B1 | 4/2002 | Lockemeyer | 502/347 |
| 6,579,825 B2 | 6/2003 | Lockemeyer | 502/347 |
| 6,656,874 B2 | 12/2003 | Lockemeyer | 502/347 |

FOREIGN PATENT DOCUMENTS

| | | |
|---|---|---|
| EP | 211521 | 2/1987 |
| EP | 563414 A1 | 10/1993 |
| EP | 716884 | 6/1996 |
| EP | 0937498 A1 | 8/1999 |
| FR | 2005978 | 10/1969 |
| GB | 568978 | 4/1945 |
| JP | 56105750 | 8/1981 |
| JP | 56164013 | 12/1981 |
| WO | 86/06063 | 10/1986 |
| WO | 95/11953 | 5/1995 |
| WO | 96/23585 | 8/1996 |
| WO | 96/41848 | 12/1996 |

OTHER PUBLICATIONS

Pending U.S. Appl. No. 10/936,249, filed Sep. 8, 2004, Lockemeyer.

Pending U.S. Appl. No. 10/935,841, filed Sep. 8, 2004, Lockemeyer.

Brunauer, S., Emmett, P. Y. and Teller, E., J. Am. Chem. Soc., 60, 309-16 (1938).

International Preliminary Examination Report, dated Aug. 17, 2000, for PCT/EP99/06725 (WO 00/15335) (TH1396 PCT).

International Preliminary Examination Report, dated Dec. 4, 2000, for PCT/EP99/06721 (WO 00/15333) (TH1121 PCT).

International Preliminary Examination Report, dated Dec. 4, 2000, for PCT/EP/99/06722 (WO 00/15334) (TH1395 PCT).

Thomas, Charles L., "Catalytic Processes and Proven Catalysts", p. 307-309 (MIR Publishing House 1973) (English Translation provided).

E.P.O. Communication, dated Nov. 25, 2005, for E.P.C. Patent Application 99 944 639.6 (TH1121 EPC).

* cited by examiner

CATALYST COMPOSITION

This application is a continuation-in-part of U.S. patent application Ser. No. 09/992,784 filed Nov. 6, 2001, the entire disclosure of which is hereby incorporated by reference, which is a continuation of U.S. patent application Ser. No. 09/392,521 filed Sep. 9, 1999, now abandoned, the entire disclosure of which is hereby incorporated by reference, which claims the benefit of U.S. Provisional Application No. 60/100,196 filed Sep. 14, 1998, the entire disclosure of which is hereby incorporated by reference.

FIELD OF THE INVENTION

The invention relates to a catalyst with improved catalytic properties, particularly a catalyst suitable for the preparation of epoxides.

BACKGROUND OF THE INVENTION

Methods have been described for lowering the total concentration of soluble species in the bulk of a catalyst carrier. These methods generally involve a process by which the carrier is manufactured in such a way so as to lower the concentration of those species throughout the bulk of the carrier. These approaches limit the formulation of carriers, often times with undesirable consequences such as high carrier density.

U.S. Pat. No. 4,797,270 discloses water washing to reduce the sodium content of an alumina powder. The pH of the wash water may need to be adjusted for extraction of other metals and Japanese patent JP56164013 discloses the use of a low pH (acid) to extract uranium and thorium from a calcined α-alumina raw material.

U.S. Pat. Nos. 4,361,504 and 4,366,092 suggest that ethylene oxide catalyst be water washed after the deposition of silver or silver/gold on the carrier. EP-211521 discloses washing of a catalyst with hot water to remove basic materials left on the catalyst from a silver impregnation process or the physical deposition of alkali metals. U.S. Pat. No. 4,367,167 discloses a process for a supported catalyst wherein an impregnated support is immersed in an inert water immiscible organic solvent containing a dissolved aliphatic amine. U.S. Pat. No. 4,810,689 discloses depositing a silver compound, decomposing the silver compound to silver in the presence of an alkali metal compound, removing organic deposits by washing and introducing fresh alkali metal by impregnation during or after the washing stage. U.S. Pat. Nos. 4,186,106 and 4,125,480 disclose washing with an inert liquid after deposition of the catalytic metal and before deposition of a promoter material.

The prior art remains concerned with the total amount of impurities; i.e., impurities throughout the bulk. Unfortunately, the impurity removal techniques taught typically attack the carrier itself. It has surprisingly been found that controlling the solubilization rate of certain species found on a carrier surface results in a catalyst with improved catalytic properties.

SUMMARY OF THE INVENTION

According to the invention, there is provided a catalyst carrier comprising a material having a sodium solubilization rate no greater than 5 ppmw/5 minutes.

Another embodiment of the invention provides a catalyst comprising a carrier having a sodium solubilization rate no greater than 5 ppmw/5 minutes; and one or more catalytically reactive metals deposited on said carrier.

A further embodiment of the invention provides a catalyst suitable for the vapor phase production of epoxides comprising a carrier having a sodium solubilization rate no greater than 5 ppmw/5 minutes; and one or more catalytically reactive metals deposited on said carrier.

A further embodiment of the invention provides a catalyst suitable for the vapor phase production of oxiranes from olefin and oxygen comprising a carrier having a sodium solubilization rate no greater than 5 ppmw/5 minutes; and catalytically reactive silver deposited on said carrier.

DETAILED DESCRIPTION

It has been found that carriers which have a controlled solubilization rate, in particular controlled sodium and/or soluble silicate solubilization rates, provide catalysts with improved catalytic properties, such as activity, selectivity and activity and/or selectivity performance over time. Controlling the solubilization rate is believed to work to improve the properties of most catalysts, no matter how impure the bulk carrier material. Further, controlling the solubilization rate will work for organic or inorganic carriers.

The typical carrier of the invention has a sodium solubilization rate in boiling water which is controlled to be no greater than 5 ppmw/5 minutes. As used herein, boiling water is deemed to have a temperature of 100° C. "Solubilization rate" as used herein refers to the measurable solubilization rate of the sodium in a solution after the carrier is placed in the solution for a specified time and at a ratio of boiling solution to carrier of 3:1. Thus, a solubilization rate in boiling water of 5 ppmw sodium/5 minutes is the amount of sodium measured in the water after the carrier has been in the boiling water for five minutes.

Carriers are commonly inorganic materials such as, for example, alumina-, silica-, or titania-based compounds, or combinations thereof, such as alumina-silica carriers. Carriers may also be made from carbon-based materials such as, for example, charcoal, activated carbon, or fullerenes. Ionizable species typically present on the inorganic type carriers include sodium, potassium, aluminates, soluble silicate, calcium, magnesium, aluminosilicate, cesium, lithium, and combinations thereof. Of particular concern are the ionizable anionic species present on the surface, particularly ionizable silicates. The solubilization rate of silicates may be measured by inductively coupled plasma (ICP) techniques and the amount of silicon species on a surface may be measured by x-ray photoelectron spectroscopy (XPS); however, since sodium is soluble in the same solutions that silicates are soluble in, the solubilization rate of sodium becomes a simpler check of the ionic species removal and it has been chosen as the indicator to define the present invention. Another measurement technique is to measure the electrical conductivity of the treatment solution.

Control of the solubilization rate may be obtained by a multiple of means. The raw materials for the carrier can be tightly controlled, for example. Or the surface of the carrier may be treated. As used herein, the "surface" of the carrier is that area of the carrier which may be measured by BET analysis. Specifically, the surface of the carrier is the site at which reaction takes place. Lowering the concentration of ionizable species on the surface of the carrier has been found to be an effective and cost efficient means of achieving the desired sodium solubilization rate. An "ionizable" species is a species which is capable of being rendered ionic, where the term "ionic" or "ion" refers to an electrically charged chemical moiety.

Lowering the surface solubilization rate of ionizable species may be accomplished by any means (i) which is effective in rendering the ionizable species ionic and removing the species, or (ii) which renders the ionizable species insoluble, or (iii) which renders the ionizable species immobile; however, use of aggressive medias is discouraged as these medias tend to dissolve the carrier, extract too much material from the bulk, and generate acidic or basic sites in the pores. Acids, which are considered aggressive media, will remove the cations on a carrier but are fairly ineffectual in removing the undesirable anions, such as silicates. Effective means of lowering concentration include washing the carrier; ion exchange; volatilizing, precipitating, or sequestering the impurities; causing a reaction to make the ionizable species on the surface insoluble; and combinations thereof. The bulk carrier may be treated, or the raw materials used to form the carrier may be treated before the carrier is manufactured. Even greater improvements in solubilization rate control are seen when both the carrier raw materials and the finished carrier are treated.

In an embodiment, amongst others, a base may be deposited on the carrier before depositing catalyst ingredients on the carrier, such as silver. The base may be deposited on the carrier by impregnating the carrier with an aqueous solution containing an amount of the base. A suitable base may be hydroxide, for example lithium hydroxide, tetramethylammonium hydroxide or tetraethylammonium hydroxide. The amount of base may be, for example, 10, 14, 20 or 30 mmole/kg carrier. The volume of impregnation solution may be such that the carrier is impregnated until a point of incipient wetness of the carrier has been reached. Alternatively, a larger volume may be used and the surplus of solution may be removed from the wet carrier by centrifugation. After impregnation, the carrier may be dried in a stream of air, for example at 250° C., for a sufficient period of time, for example 5.5 minutes.

To make a catalyst from the carrier, the carrier is typically impregnated with metal compound(s), complex(es) and/or salt(s) dissolved in a suitable solvent sufficient to deposit or impregnate a catalytically effective amount of metal on the carrier. As used herein, "catalytically effective amount" means an amount of metal that provides a measurable catalytic effect. For example, a catalytically effective amount of metal when referring to an olefin epoxidation catalyst is that amount of metal which provides a measurable conversion of olefin and oxygen to alkylene oxide. In addition, one or more promoters may also be deposited on the carrier either prior to, coincidentally with, or subsequent to the deposition of the catalytically reactive metal. The term "promoter" as used herein refers to a component which works effectively to provide an improvement in one or more of the catalytic properties of the catalyst when compared to a catalyst not containing such component.

Further improvement in the catalyst properties are seen when the metal deposition is effected by contacting the carrier with an impregnation solution whose hydrogen ion activity has been lowered. "Hydrogen ion activity" as used herein is the hydrogen ion activity as measured by the potential of a hydrogen ion selective electrode. As used herein, a solution with "lowered" hydrogen ion activity refers to a solution whose hydrogen activity has been altered by the addition of a base, such that the hydrogen ion activity of the altered solution is lowered compared to the hydrogen ion activity of the same solution in an unaltered state. The base selected to alter the solution may be chosen from any base or compound with a pKb lower than the original impregnation solution. It is particularly desirable to chose a base which does not alter the formulation of the impregnation solution; i.e., which does not alter the desired metals concentration in the impregnation solution and deposited on the carrier. Organic bases will not alter the impregnation solution metals concentrations, examples of which are tetraalkylammonium hydroxides and 1,8-bis-(dimethylamino)-naphthalene. If changing the metals concentration of the impregnation solution is not a concern, metal hydroxides may be used.

When the impregnation solution is at least partially aqueous, an indication of the change in the hydrogen activity may be measured with a pH meter, with the understanding that the measurement obtained is not pH by a true, aqueous definition. "Measured pH" as used herein shall mean such a non-aqueous system pH measurement using a standard pH probe. Even small changes in the "measured pH" from the initial impregnation solution to that with added base are effective and improvements in catalytic properties continue as the "measured pH" change increases with base addition. High base additions do not seem to adversely affect catalyst performance; however, high additions of hydroxides have been seen to cause sludging of the impregnation solution, creating manufacturing difficulties. When the base addition is too low, the hydrogen ion activity will not be affected. The hydrogen ion activity lowering procedure is also quite effective when used by itself; i.e., when no ionizable species concentrations are lowered prior to impregnation.

The impregnated carrier, also known as a catalyst precursor, is dried in the presence of an atmosphere which also reduces the catalytic metal. Drying methods known in the art include steam drying, drying in an atmosphere with a controlled oxygen concentration, drying in a reducing atmosphere, air drying, and staged drying using a suitable ramped or staged temperature curve.

By way of example, the invention will be described in more detail for a catalyst suitable for the vapor phase production of epoxides, also known as an epoxidation catalyst.

An epoxidation catalyst typically comprises an inorganic carrier, such as for example, and alumina-based carrier such as α-alumina, with one or more catalytically reactive metals deposited on the carrier. The carrier typically contains certain ionizable species, for example an α-alumina carrier, typically contains species including sodium, potassium, aluminates, soluble silicates, calcium, magnesium, aluminosilicates, and combinations thereof. It has been found that silicates, and certain other anions, are particularly undesirable ionizable species in an epoxidation catalyst. As already described, the solubilization rate of silicons/silicates may be measured by ICP and by XPS; however, since sodium is soluble in the same solutions that silicates are soluble in, the solubilization rate of sodium becomes a simpler check of the ionic species removal. Another measurement technique is to measure the electrical conductivity of the treatment solution.

According to the invention, the sodium solubilization rate of the carrier is controlled. The solubilization rate may be controlled by lowering the concentration of ionizable species on the surface. Ionizable species concentration may be lowered by means which render the ionizable species ionic and thereafter removing the ionic species, or by rendering those ionizable species insoluble, or rendering the ionizable species immobile. For example, the carrier, or the raw materials of the carrier, may be subjected to washing; ion exchange; volatilizing, precipitating, or sequestering the impurities; causing a reaction to make the ionizable species on the surface insoluble; and combinations thereof. When washing is used, the sodium solubilization rate in 3:1 w/w boiling water is preferably controlled to less than 5 ppmw Na/5 minutes.

The carrier having the controlled solubilization rate is impregnated with metal ions or compound(s), complex(es) and/or salt(s) dissolved in a suitable solvent sufficient to cause the desired deposition on the carrier. When silver is the deposition material, a typical deposition is from about 1 to about 40 percent by weight, preferably from about 1 to about 30 percent by weight silver, basis the weight of the total catalyst. The impregnated carrier is subsequently separated from the solution and the deposited metal(s) compound is reduced to metallic silver.

One or more promoters may be deposited either prior to, coincidentally with, or subsequent to the deposition of the metal. Promoters for epoxidation catalysts are typically selected from sulfur, phosphorus, boron, fluorine, Group IA through Group VIII metals, rare earth metals, and combinations thereof. The promoter material is typically compound(s) and/or salt(s) of the promoter dissolved in a suitable solvent.

For olefin epoxidation catalysts, Group IA metals are typically selected from potassium, rubidium, cesium, lithium, sodium, and combinations thereof; with potassium and/or cesium and/or rubidium being preferred. Even more preferred is a combination of cesium plus at least one additional Group IA metal, such as cesium plus potassium, cesium plus rubidium, or cesium plus lithium. Group IIA metals are typically selected from magnesium, calcium, strontium, barium, and combinations thereof, Group VIII transition metals are typically selected from cobalt, iron, nickel, ruthenium, rhodium, palladium, and combinations thereof; and rare earth metals are typically selected from lanthanum, cerium, neodymium, samarium, gadolinium, dysprosium, erbium, ytterbium, and mixtures thereof. Non-limiting examples of other promoters include perrhenate, sulfate, molybdate, tungstate, chromate, phosphate, borate, sulfate anion, fluoride anion, oxyanions of Group IIIB to VIB, oxyanions of an element selected from Groups III through VIIB, alkali(ne) metal salts with anions of halides, and oxyanions selected from Groups IIIA to VIIA and IIIB through VIIB. The amount of Group IA metal promoter is typically in the range of from about 10 ppm to about 1500 ppm, expressed as the metal, by weight of the total catalyst, and the Group VIIb metal is less than about 3600 ppm, expressed as the metal, by weight of the total catalyst.

For further improvement in catalytic properties, the hydrogen ion activity of the impregnation solution is optionally lowered, such as by the addition of a base. The typical known impregnation solution for an epoxidation catalyst is quite basic, so a strong base is used to further lower the hydrogen ion activity. Examples of strong bases include alkyl ammonium hydroxide such as tetraethylammonium hydroxide, and metal hydroxide such as lithium hydroxide and cesium hydroxide. In order to maintain the desired impregnation solution formulation and metal loading, an organic base such as tetraethylammonium hydroxide is preferred. Base additions in these systems typically result in a "measured pH" change ranging up to about 3 pH units, realizing that the "measured pH" is not a true pH since the impregnation system is not aqueous.

In certain embodiments, amongst others, silver may be deposited on the carrier in two or more portions. If, as promoters, perrhenate is used in conjunction with tungstate, a portion of silver may advantageously be deposited together with the deposition of the tungstate, and another portion of silver may subsequently be deposited together with the deposition of the perrhenate.

The carrier employed in these catalysts in its broadest aspects can be any of the large number of conventional, porous refractory catalyst carriers or carrier materials which are considered relatively inert. Such conventional materials are known to those skilled in the art and may be of natural or synthetic origin. Carriers for epoxidation catalysts are preferably of a macroporous structure and have a surface area below about 10 $m^2/g$ and preferably below about 3 $m^2/g$. Examples of carriers for different catalysts are the aluminum oxides (including the materials sold under the trade name "Alundum"), charcoal, pumice, magnesia, zirconia, kieselguhr, fuller's earth, silicon carbide, porous agglomerates comprising silica and/or silicon carbide, silica, magnesia, selected clays, artificial and natural zeolites, alkaline earth carbonates, and ceramics. Refractory carriers especially useful in the preparation of olefin epoxidation catalysts comprise the aluminous materials, in particular those comprising α-alumina. In the case of α-alumina-containing carriers, preference is given to those having a specific surface area as measured by the B.E.T. method of from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$, and a water pore volume as measured by conventional water absorption techniques of from about 0.1 to about 0.75 cc/g by volume. The B.E.T. method for determining specific surface area is described in detail in Brunauer, S., Emmett, P. Y. and Teller, E., *J. Am. Chem. Soc.*, 60, 309–16 (1938).

Certain types of α-alumina containing carriers are particularly preferred. These α-alumina carriers have relatively uniform pore diameters and are more fully characterized by having B.E.T. specific surface areas of from about 0.1 $m^2/g$ to about 3 $m^2/g$, preferably from about 0.1 $m^2/g$ to about 2 $m^2/g$, and water pore volumes of from about 0.10 cc/g to about 0.55 cc/g. Manufacturers of such carriers include Norton Chemical Process Products Corporation and United Catalysts, Inc. (UCI).

The resulting epoxidation catalysts just described are used for the vapor phase production of epoxides. A typical epoxidation process involves loading catalysts into a reactor. The feedstock to be converted, typically a mixture of ethylene, oxygen, carbon dioxide, nitrogen and ethyl chloride, is passed over the catalyst bed at pressure and temperature. The catalyst converts the feedstock to an outlet stream product which contains ethylene oxide. Nitrogen oxides ($NO_x$) may also be added to the feedstock to boost catalyst conversion performance.

Having generally described the invention, a further understanding may be obtained by reference to the following examples, which are provided for purposes of illustration only and are not intended to be limiting unless otherwise specified.

EXAMPLES

Carriers

The properties of the carriers used in Examples 1–11 are given in Table I.

TABLE I

| Carrier | A | B | C | D |
|---|---|---|---|---|
| B.E.T. Surface Area (m$^2$/g) [a] | 0.84 | 0.97 | 0.78 | 0.87 |
| Water Absorption (%) | 39.7 | 46.2 | 37.6 | 43.4 |
| Crush Strength (kg) [b] | 6.53 | 8.07 | 12.29 | 5.44 |
| Total Pore Volume (cc/g) [c] | 0.408 | 0.460 | 0.390 | |
| Median Pore Diameter (microns) [c] | 1.8 | 2.7 | 1.3 | |
| SiO$_2$ (% w) | 0.5 | 0.8 | 0.1 | 0.5 |
| Bulk Acid-Leachable Na (ppmw) | 438 | 752 | 186 | 339 |
| Bulk Acid-Leachable K (ppmw) | 85 | 438 | 109 | 37 |
| Bulk Acid-Leachable Ca (ppmw) | 207 | 508 | 526 | 123 |
| Bulk Acid-Leachable Al (ppmw) | 744 | 1553 | 657 | 499 |
| Bulk Acid-Leachable SiO$_2$ (ppmw) | 808 | 1879 | 1560 | 600 |
| alpha-Alumina (% w) | Bal | Bal | Bal | Bal |

[a] Method of Brunauer, Emmett and Teller, loc. cit.
[b] Flat Plate Crush Strength, single pellet.
[c] Determined by mercury intrusion to 3.8 × 10$^8$ Pa using Micromeritics Autopore 9200 or 9210 (130° contact angle, 0.473 N/m surface tension of Hg).

Carrier Water Washing Procedures for Examples 1, 2, 3, 4, 6, 7, 10, 12

Carrier washing was carried out by immersing 100 grams of carrier in 300 grams of boiling de-ionized water for 15 minutes. The carrier was then removed and placed in a fresh 300 grams of boiling water for another 15 minutes. This procedure was repeated once more for a total of three immersions, at which point the carrier was separated from the water and dried in a well ventilated oven at 150° C. for 18 hours. The dried carrier was then used for preparation of a catalyst by the procedures outlined in the following Examples.

Impregnation Solution

A silver-amine-oxalate stock solution was prepared by the following procedure:

415 g of reagent-grade sodium hydroxide were dissolved in 2340 ml de-ionized water and the temperature was adjusted to 50° C. 1699 g high purity "Spectropure" silver nitrate were dissolved in 2100 ml de-ionized water and the temperature was adjusted to 50° C.

The sodium hydroxide solution was added slowly to the silver nitrate solution, with stirring, while maintaining a solution temperature of 50° C. The mixture was stirred for 15 minutes, then the temperature was lowered to 40° C.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml fresh deionized water was then added. 630 g of high-purity oxalic acid dihydrate were added in approximately 100 g increments. The temperature was keep at 40° C. and the pH was kept above 7.8.

Water was removed from the mixture to leave a highly concentrated silver-containing slurry. The silver oxalate slurry was cooled to 30° C. 699 g of 92% w ethylenediamine (8% de-ionized water) was added while maintaining a temperature no greater than 30° C. The resulting solution contained approximately 27–33% w silver.

Enough 45% w aqueous CsOH and water was added to this solution to give a finished catalyst having 14.5% w silver and a desired cesium loading (see Examples).

Sodium Measurement Procedures

The sodium solubilization rate of selected carriers was determined by measuring the sodium content of the extracting medium with an Orion model no. 8611BN sodium selective electrode connected to an Orion model 290A voltmeter, and by XPS. The silicate solubilization rates were measured by XPS. In a typical experiment, 300 grams of carrier was boiled in 900 grams of de-ionized water for a total of fifteen minutes. During this period, 3 ml aliquots were taken at predetermined intervals. The sodium content of each aliquot was analyzed at 25° C. using procedures well established for ion selective electrodes. The sodium concentration in the solution sampled at 5 minutes is used to evaluate the carrier as being a good or poor candidate for catalyst preparation. Results are given in Table II.

TABLE II

Sodium Solubilization Rates for Selected α-Alumina Carriers

| Carrier | Bulk Na Unwashed Carrier (ppmw)[a] | Extracted Na Unwashed Carrier (ppmw) | Extracted Na Washed Carrier (ppmw) |
|---|---|---|---|
| A | 438 | 9.2 | 1.3 |
| A[b] | 438 | 9.2 | 1.2 |
| B | 752 | 9.2 | 1.8 |
| C | 186 | 10.2 | — |

[a] From Table I.
[b] Following ammonium acetate exchange as described in Example 8.

pH Measurement Procedures

Silver solution pH measurements were done using a Metrohm model 744 pH meter, employing a model 6.0220.100 combination electrode and a Pt 100 model 6.1110.100 resistance thermometer for temperature compensation. The meter was calibrated with commercially available buffer solutions before each use. In a typical measurement, a 50 cc aliquot of the doped silver solution to be used for a catalyst impregnation was filtered into a 100 cc glass beaker through a 2 micron filter attached in-line to a plastic syringe. The pH probe was lowered into the magnetically stirred solution, and the reading obtained after 3 minutes was recorded as the equilibrated pH. The probe was cleaned between each measurement with deionized water, and checked for calibration. Special care was taken to prevent accumulation of AgCl solids on the electrode membrane. Such accumulation was removed by soaking the probe in ammonium hydroxide solution, as recommended by the manufacturer.

Example 1

A catalyst pre-cursor was prepared from Carrier A by first subjecting the carrier to carrier washing. Following the wash, approximately 30 grams of washed Carrier A were placed under a 25 mm Hg vacuum for 1 minute at ambient temperature. Approximately 50 grams of the impregnating solution was then introduced to submerse the carrier, and the vacuum was maintained at 25 mm Hg for an additional 3 minutes. The cesium target was 450 ppmw/gram finished catalyst. The vacuum was then released and the excess impregnating solution was removed from the catalyst pre-cursor by centrifugation at 500 rpm for two minutes. The catalyst pre-cursor was then dried while being shaken at 240° C. for 4 minutes in a stream of air flowing at 11.3 m$^3$/hr.

Example 1a (Comparative)

Carrier A was impregnated as described in Example 1; however, the carrier was not subjected to carrier washing. The cesium target was 400 ppmw/gram finished catalyst.

Example 2

Carrier B was subjected to carrier washing and impregnation as described in Example 1. The cesium target was 450 ppmw/gram finished catalyst.

Example 2a (Comparative)

Carrier B was impregnated as described in Example 1; however, the carrier was not subjected to carrier washing. The cesium target was 400 ppmw/gram finished catalyst.

Example 3

Carrier C was subjected to carrier washing and impregnation as described in Example 1. The cesium target was 300 ppmw/gram finished catalyst.

Example 3a (Comparative)

Carrier C was impregnated as described in Example 1; however, the carrier was not subjected to carrier washing. The cesium target was 360 ppmw/gram finished catalyst.

Example 4

Carrier A was subjected to carrier washing and impregnation as described in Example 1. The cesium target was 450 ppmw/gram finished catalyst. In addition, 35% aqueous tetraethylammonium hydroxide (TEAH) was added to the stock impregnation solution at a target of 117.8 micromoles $OH^-$/cc Ag, to lower the hydrogen ion activity to a "measured pH" of 13.2.

Example 5

100 g of Carrier A were immersed in 300 ml of boiling 5% w TEAH for 15 min, then immersed six times in 300 ml of boiling de-ionized water for 15 minutes each. The carrier was then removed and dried in a well ventilated oven at 150° C. for 18 hours. The carrier was then impregnated with a cesium target of 400 ppmw/gram finished catalyst. In addition, 35% w TEAH was added to the stock impregnation solution at a target of 117.8 micromoles $OH^-$/cc Ag, to lower the hydrogen ion activity to a "measured pH" of 13.6.

Example 6

Carrier A was subjected to carrier washing and impregnation as described in Example 1. The cesium target was 720 ppmw/gram finished catalyst. In addition, TEAH was dissolved in water and added to the stock solution at a target of 117.8 micromoles $OH^-$/cc Ag, to lower the hydrogen activity to a "measured pH" of 13.2, and $NH_4ReO_4$ was dissolved in water and added to the stock solution to provide 1.5 micromoles Re/gram finished catalyst.

Example 7

Carrier A was subjected to carrier washing and impregnation as described in Example 1. The cesium target was 450 ppmw/gram finished catalyst. In addition, LiOH was dissolved in water and added to the stock impregnation solution to lower the hydrogen ion activity to a "measured pH" of 13.2.

Example 7a (Comparative)

Carrier A was impregnated as described in Example 7; however, the carrier was not subjected to carrier washing. The cesium target was 400 ppmw/gram finished catalyst.

Example 8

300 g of Carrier A were immersed in 900 ml of a boiling 0.1 M solution of ammonium acetate for 15 min, then immersed in 300 ml of de-ionized water at 25° C. for 15 minutes, followed by immersion three times in 300 ml of boiling de-ionized water for 15 minutes each. The carrier was then removed and dried in a well ventilated oven at 150° C. for 18 hours. The carrier was then impregnated as described in Example 1. The cesium target was 450 ppmw/gram finished catalyst. In addition, LiOH was dissolved in water and added to the stock impregnation solution to lower the hydrogen ion activity to a "measured pH" of 13.2.

Example 9

The α-alumina source material for Carrier A was washed with de-ionized water at 25° C., then homogenized with the same ingredients used to form Carrier A before extruding, drying, and firing in a muffle furnace. The resulting carrier was designated Carrier D. Carrier D was used to prepare a catalyst in the same manner as described in Example 1. The cesium target was 510 ppmw/gram finished catalyst. In addition, LiOH was dissolved in water and added to the stock impregnation solution to lower the hydrogen ion activity to a "measured pH" of 13.2.

Example 9a (Comparative)

A catalyst was prepared from Carrier D in the same manner as outlined in Example 9; however, the carrier was not subjected to carrier washing. The cesium target was 360 ppmw/gram finished catalyst.

Example 10

100 g of Carrier A were immersed in 300 ml of a boiling 0.1 M solution of barium acetate at 25° C. for 15 min, then immersed in 300 ml of de-ionized water at 25° C. for 15 minutes, followed by immersion three times in 300 ml of boiling de-ionized water for 15 minutes each. The carrier was then removed and dried in a well ventilated oven at 150° C. for 18 hours. The carrier was then impregnated as described in Example 1. The cesium target was 400 ppmw/gram finished catalyst. In addition, LiOH was dissolved in water and added to the stock impregnation solution to lower the hydrogen ion activity to a "measured pH" of 13.2.

Example 11

Carrier A was subjected to carrier washing and impregnation as described in Example 1. The cesium target was 650 ppmw/gram finished catalyst. In addition, LiOH was dissolved in water and added to the stock impregnation solution to lower the hydrogen ion activity to a "measured pH" of 13.2 and $NH_4ReO_4$ was dissolved in water and added to the stock impregnation solution to provide 1.5 micromoles Re/gram finished catalyst.

The catalysts of Examples 1–11 were used to produce ethylene oxide from ethylene and oxygen. 3 to 5 grams of crushed catalyst were loaded into a 6.35 mm inside diameter stainless steel U-shaped tube. The U tube was immersed in a molten metal bath (heat medium) and the ends were connected to a gas flow system. The weight of the catalyst used and the inlet gas flow rate were adjusted to achieve a gas hourly space velocity of 6800 cc of gas per cc of catalyst per hour. The inlet gas pressure was 1450 kPa.

The gas mixture passed through the catalyst bed (in a once-through operation) during the entire test run (including start-up) consisted of 25% ethylene, 7.0% oxygen, 5% carbon dioxide, 63% nitrogen, and 2.0 to 6.0 ppmv ethyl chloride.

The initial reactor (heat medium) temperature was 180° C. The temperature was ramped at a rate of 10° C. per hour from 180° C. to 225° C., and then adjusted so as to achieve a constant ethylene oxide level of 1.5% v in the outlet gas stream. Performance data at this conversion level are usually obtained when the catalyst has been on stream for a total of at least 1–2 days. Due to slight differences in feed gas composition, gas flow rates, and the calibration of analytical instruments used to determine the feed and product gas compositions, the measured selectivity and activity of a given catalyst may vary slightly from one test run to the next.

The initial performance values for selectivity at 1.5% ethylene oxide were measured and are reported in Table III.

best illustrated in Examples 6 and 11, where a selectivity enhancing dopant, such as rhenium, is added to the impregnating solution.

Example 12

An impregnation solution was prepared by adding aqueous solutions comprising lithium hydroxide, cesium hydroxide, and water to samples of an silver-amine-oxalate stock solution. The amounts of lithium hydroxide and cesium hydroxide were 70 mmole/kg and 4 mmole/kg, respectively, relative to the weight of the carrier. The measured pH (as measured at 20° C.) of the impregnation solution was 14.6. The silver-amine-oxalate stock solution was prepared as described in U.S. Pat. No. 4,766,105, which is incorporated herein by reference.

A sample of an α-alumina carrier having a surface area of 0.87 $m^2/g$ and a water absorption of 0.42 g/g was washed with water following the procedures outlined hereinbefore, and dried. Subsequently, the carrier impregnated with the impregnation solution and dried, as follows. The carrier sample (approximately 30 g) was placed under a 25 mm Hg vacuum for 1 minute at ambient temperature. Approximately 50 g of the impregnating solution, prepared as indicated hereinbefore, was then introduced to submerse the carrier,

TABLE III

Performance Characteristics of Catalysts Prepared From Unwashed and Washed α-Alumina

| Example | Carrier | Pre-Impregnation Condition | Base Addition | Impregnating Solution "measured pH" | Selectivity (%) | Temperature (° C.) |
|---|---|---|---|---|---|---|
| 1 | A | water wash | none | 11.2 | 82.7 | 229 |
| 1a | A | no wash | none | 11.2 | 81.3 | 237 |
| 2 | B | water wash | none | 11.2 | 82.5 | 226 |
| 2a | B | no wash | none | 11.2 | 82.0 | 232 |
| 3 | C | water wash | none | 11.2 | 82.0 | 229 |
| 3a | C | no wash | none | 11.2 | 82.0 | 235 |
| 4 | A | water wash | TEAH | 13.2 | 82.7 | 226 |
| 5 | A | TEAH wash + water wash | TEAH | 13.6 | 82.7 | 222 |
| 6 | A | water wash | TEAH | 13.2 | 89.4 | 245 |
| 7 | A | water wash | LiOH | 13.2 | 82.7 | 226 |
| 7a | A | no wash | LiOH | 13.2 | 82.0 | 227 |
| 8 | A | Ammonium acetate wash | LiOH | 13.2 | 83.1 | 222 |
| 9 | D | raw material wash + carrier body wash | LiOH | 13.2 | 82.7 | 222 |
| 9a | D | raw material wash + no carrier body wash | LiOH | 13.2 | 83.0 | 225 |
| 10 | A | barium acetate wash | LiOH | 13.2 | 82.7 | 226 |
| 11 | A | water wash | LiOH | 13.2 | 86.2 | 232 |

It can be seen that significant improvement in catalyst properties are seen when the sodium solubilization rate is lowered. Carriers A and B have dramatically lower sodium solubilization rates (see Table II) after being subjected to the Carrier Washing Procedure. Notice that despite the lower bulk sodium for Carrier C, it has a high sodium solubilization rate. Even further improvement is seen when the material used to make the carrier is washed before the carrier is formed, Carrier D.

The hydrogen ion activity of the deposition solution for catalysts in Examples 4–11 was lowered by the addition of a base. It can be seen that lowering the hydrogen ion activity of the deposition solution further improves the catalytic properties. It is also evident that the phenomenon of the pH effect is not restricted to a particular catalyst formulation, as and the vacuum was maintained at 25 mm Hg for an additional 3 minutes. The vacuum was then released and the excess impregnating solution was removed from the catalyst pre-cursor by centrifugation at 500 rpm for two minutes. The catalyst pre-cursor was then dried while being shaken at 250° C. for 5.5 minutes in a stream of air. The catalyst prepared contained 14.5% w silver, 60 mmole/kg lithium, and 3.4 mmole/kg cesium, relative to the weight of the catalyst.

The catalyst so prepared was tested in the production of ethylene oxide from ethylene and oxygen. To do this, 1.68 g of crushed catalyst was loaded into a stainless steel U-shaped tube. The tube was immersed in a molten metal bath (heat medium) and the ends were connected to a gas flow system. A gas or gas mixture passed through the catalyst bed, in a "once-through" operation. The weight of catalyst used and the inlet gas flow rate were adjusted to give a gas hourly space velocity of 6800 Nml of gas per ml catalyst per hour, as calculated for uncrushed catalyst. The inlet gas pressure was 1450 kPa.

The gas mixture contained 30% v ethylene, 8% v oxygen, 5% v carbon dioxide, 2.5 ppmv ethyl chloride, and nitrogen balance.

The reactor temperature was ramped up at a rate of 10° C. per hour to 225° C. and then the temperature was adjusted so as to achieve an ethylene oxide content of 1.5% v in the outlet gas stream. The ethyl chloride concentration in the gas mixture was adjusted between 2.5 and 5 ppmv so as to obtain an optimum selectivity at a constant ethylene oxide concentration in the outlet gas stream. The temperature was slowly increased to compensate for a decline in catalyst performance as a result of ageing, i.e. such that a constant ethylene oxide content in the outlet gas stream was maintained.

The initial performance of the catalyst (i.e. after the catalyst had been on stream for at least 1–2 days) was as follows: the selectivity was 82.4%, the activity expressed as the temperature needed to achieve an ethylene oxide content of 1.5% v in the outlet gas stream was 222° C.

The stability of the catalyst was evaluated as follows. A sample of the crushed catalyst (0.808 g) was loaded in a 3.6 mm inside diameter stainless steel U-shaped tube. The tube was immersed in a molten metal bath (heat medium) and the ends were connected to a gas flow system. A gas or gas mixture passed through the catalyst bed, in a "once-through" operation. The weight of catalyst used and the inlet gas flow rate were adjusted to give a gas hourly space velocity of 30000 Nml of gas per ml catalyst per hour, as calculated for uncrushed catalyst. The inlet gas pressure was 1450 kPa. The gas mixture contained 30% v ethylene, 8% v oxygen, 5% v carbon dioxide, 5.6 ppmv ethyl chloride, and nitrogen balance.

The reactor temperature was ramped up at a rate of 10° C. per hour to 245° C. and then the temperature was adjusted so as to achieve an oxygen conversion level of 25%.

After reaching the initial performance level of the catalyst (initial selectivity was 80.9%; initial activity was 247° C., expressed as the temperature needed to achieve an oxygen conversion level of 25%), the temperature was slowly increased to compensate for a decline in catalyst performance as a result of ageing, i.e. such that a constant oxygen conversion was maintained. There was a decline in catalyst performance in two stages. In the first stage the rate of decline in catalyst performance was substantially lower than in the second stage. In the first stage, virtually no catalyst selectivity decline was observed. In the second stage, starting at a cumulative ethylene oxide production of 1.6 kton/m$^3$ catalyst, the selectivity decline followed a substantially linear fashion, at a rate of about 1.56% per kton/m$^3$ catalyst.

It will be apparent to one of ordinary skill in the art that many changes and modifications may be made to the invention without departing from its spirit or scope as set forth herein.

What is claimed is:

1. A process for preparing a catalyst suitable for the vapor phase production of epoxides, said process comprising:
    selecting a carrier;
    lowering a concentration of one or more ionizable species present on a surface of said carrier, wherein said ionizable species comprise silicates;
    depositing on said carrier a catalytically effective amount of one or more catalytically reactive metals comprising silver in an amount of from about 1 to about 40 percent by weight, basis weight of the total catalyst; and
    depositing one or more promoters selected from phosphorus, boron, fluorine, lithium, sodium, rubidium, Group IIA through Group VIII metals, rare earth metals, and combinations thereof prior to, coincidentally with, or subsequent to the deposition of said one or more catalytically reactive metals.

2. A process according to claim 1 wherein said concentration of one or more ionizable species is lowered by a means effective in rendering the ionizable species ionic and removing that species, or rendering the ionizable species insoluble, or rendering the ionizable species immobile.

3. A process according to claim 2 wherein said means is selected from washing, ion exchange, volatilization, precipitation, sequestration, and combinations thereof.

4. A process according to claim 3 wherein said concentration of one or more ionizable species is lowered by washing with an aqueous and/or organic solvent-based solution.

5. A process according to claim 1 further comprising a drying step following said concentration lowering step.

6. A process according to claim 1 wherein said metal deposition is effected by submersing said carrier in an impregnation solution wherein a hydrogen ion activity of said solution is lowered.

7. A process according to claim 6 wherein said hydrogen ion activity is lowered by addition of a base to said impregnation solution.

8. A process according to claim 1 further comprising a drying step following the deposition step.

9. A process according to claim 1 further comprising selecting one or more carrier forming materials and lowering a concentration of one or more ionizable species present in at least one of said one or more materials prior to forming said materials into said carrier.

10. A process according to claim 1 wherein the one or more promoters comprise lithium.

11. A process according to claim 10 wherein the one or more promoters comprise in addition cesium.

12. A process according to claim 1 wherein the one or more promoters are selected from phosphorus, boron, fluorine, Group IIA through Group VIII metals, rare earth metals, and combinations thereof.

13. A process according to claim 12 wherein said Group IIA metal is selected from magnesium, calcium, strontium, barium, and combinations thereof.

14. A process according to claim 12 wherein said Group VIII metal is selected from cobalt, iron, nickel, ruthenium, rhodium, palladium, and combinations thereof, and said rare earth metal is selected from lanthanum, cerium, neodymium, samarium, gadolinium, dysprosium, erbium, ytterbium, and combinations thereof.

15. A process according to claim 12 wherein the one or more promoters comprise rhenium.

16. A process for preparing a catalyst suitable for the vapor phase production of epoxides, said process comprising:
    selecting one or more materials;
    lowering a concentration of one or more ionizable species present in at least one of said one or more materials, wherein said ionizable species comprise silicates;
    forming a carrier comprising said one or more materials;
    optionally lowering a concentration of one or more ionizable species present on a surface of said carrier;
    depositing on said carrier a catalytically effective amount of one or more catalytically reactive metals comprising silver in an amount of from about 1 to about 40 percent by weight, basis weight of the total catalyst; and depositing one or more promoters selected from sulfur, phosphorus, boron, fluorine, Group IA through Group VIII metals, rare earth metals, and combinations thereof prior to, coincidentally with, or subsequent to the deposition of said one or more catalytically reactive metals.

17. A process according to claim 16 wherein said concentration of one or more ionizable species is lowered by a means effective in rendering the ionizable species ionic and removing that species, or rendering the ionizable species insoluble, or rendering the ionizable species immobile.

18. A process according to claim 17 wherein said means is selected from washing, ion exchange, volatilization, precipitation, sequestration, impurity control, and combinations thereof.

19. A process according to claim 18 wherein said concentration of one or more ionizable species is lowered by washing with an aqueous and/or organic solvent-based solution.

20. A process according to claim 16 wherein said metal deposition is effected by submersing said carrier in an impregnation solution wherein a hydrogen ion activity of said solution is lowered.

21. A process according to claim 20 wherein said hydrogen ion activity is lowered by addition of a base to said impregnation solution.

22. A process according to claim 16 wherein the one or more promoters comprise a Group IA metal which is selected from potassium, rubidium, cesium, sodium, and combinations thereof.

23. A process according to claim 22 wherein the one or more promoters comprise a combination of cesium and at least one additional Group IA metal which is selected from potassium, rubidium, and lithium.

24. A process according to claim 16 wherein the one or more promoters are selected from sulfur, phosphorus, boron, fluorine, Group IIA through Group VIII metals, rare earth metals, and combinations thereof.

25. A process according to claim 24 wherein said Group IIA metal is selected from magnesium, calcium, strontium, barium, and combinations thereof.

26. A process according to claim 24 wherein said Group VIII metal is selected from cobalt, iron, nickel, ruthenium, rhodium, palladium, and combinations thereof.

27. A process according to claim 24 wherein said rare earth metal is selected from lanthanum, cerium, neodymium, samarium, gadolinium, dysprosium, erbium, ytterbium, and combinations thereof.

28. A process according to claim 24 wherein the one or more promoters comprise rhenium.

* * * * *